United States Patent [19]

Lessing

[11] Patent Number: 5,459,767

[45] Date of Patent: Oct. 17, 1995

[54] METHOD FOR TESTING THE STRENGTH AND STRUCTURAL INTEGRITY OF NUCLEAR FUEL PARTICLES

[75] Inventor: Paul A. Lessing, Idaho Falls, Id.

[73] Assignee: Lockheed Idaho Technologies Company, Idaho Falls, Id.

[21] Appl. No.: 362,052

[22] Filed: Dec. 21, 1994

[51] Int. Cl.$^6$ ............................................ G21C 17/06
[52] U.S. Cl. .......................... 376/245; 73/821; 376/901; 376/430; 100/99
[58] Field of Search .................................. 376/245, 260, 376/261, 430, 901; 73/818, 821; 100/99

[56] References Cited

U.S. PATENT DOCUMENTS

| | | | |
|---|---|---|---|
| 3,771,357 | 11/1973 | Gambini | 73/821 |
| 3,994,157 | 11/1976 | Burk et al. | 73/821 |
| 4,227,081 | 10/1980 | Caputo et al. | 376/245 |
| 4,909,141 | 3/1990 | Blenski et al. | 376/260 |

OTHER PUBLICATIONS

Tennery, V. J. et al., *Structural Characterization of HTGR Pyrocarbon Fuel Particle Coatings*, Journal of American Ceramic Society, vol. 60, Nos. 5–6, pp. 268–274 (1977).

Stinton. D. P., et al., *Effect of Deposition Conditions on the Properties of Pyrolytic SiC Coatings for HTGR Fuel Particles*. Ceramic Bulletin, vol. 57, No. 6, pp. 568–573 (1978).

Krautwasser, P., et al., *Raman Spectral Characterization of Silicon Carbide Nuclear Fuel Coatings*, Journal of American Ceramic Society, vol. 66, No. 6, pp. 424–433 (1983).

Smith, C. L., *SiC–Fission Product Reactions in HTGR TRISO UC$_2$ and UC$_x$O$_y$ Fissile Fuel: I. Kinetics of Reactions in a Thermal Gradient*, Journal of American Ceramic Society, vol. 62, Nos. 11–12, pp. 600–606 (1979).

Allen, P. L., et al., *Nuclear Fuel Coated Particle Development in the Reactor Fuel Element Laboratories of the U.K. Atomic Energy Authority*, Nuclear Technology, vol. 35, pp. 346–253 (1977).

Bongartz, K., et al., *The Brittle Ring Test: A Method for Measuring Strength and Young's Modulus on Coatings of HTR Fuel Particles*, Journal of Nuclear Materials, vol. 62, pp. 123–137 (1976).

Gilchrist, K. E., et al., *A Technique for Measuring the Strength of High Temperature Reactor Fuel Particle Coatings*, Journal of Nuclear Materials, vol. 43, pp. 347–350 (1972).

Minkato, K., et al., *Crushing Strength of Irradiated TRISO Coated Fuel Particles*, Journal of Nuclear Materials, vol. 119, pp. 326–332 (1983).

Quinn, G. D., *Strength and Proof Testing*, Engineering Materials Handbook, vol, 4, pp. 585–598, ASM International (1991).

Trustrum, A. G., et al., *Applicability of Weibull Analysis for Brittle Materials*, Journal of Material Science, vol. 18, pp. 2765–2770 (1983).

Richerson, D. W., *Modern Ceramic Engineering*, Marcel Dekker, Inc., New York, Chapter 15, pp. 662–679 (1982).

Evans, A. G., *Fracture in Ceramic Materials*, Noyes Publications, Park Ridge, N.J., Chapter 15, pp. 364–402 (1984).

(List continued on next page.)

Primary Examiner—Daniel D. Wasil
Attorney, Agent, or Firm—Klaas, Law, O'Meara & Malkin

[57] ABSTRACT

An accurate method for testing the strength of nuclear fuel particles. Each particle includes an upper and lower portion, and is placed within a testing apparatus having upper and lower compression members. The upper compression member includes a depression therein which is circular and sized to receive only part of the upper portion of the particle. The lower compression member also includes a similar depression. The compression members are parallel to each other with the depressions therein being axially aligned. The fuel particle is then placed between the compression members and engaged within the depressions. The particle is then compressed between the compression members until it fractures. The amount of force needed to fracture the particle is thereafter recorded. This technique allows a broader distribution of forces and provides more accurate results compared with systems which distribute forces at singular points on the particle.

16 Claims, 5 Drawing Sheets

OTHER PUBLICATIONS

Evans, A. G., *Strength of Pyrolytic SiC Coatings of Fuel Particles for High Temperature Gas–Cooled Reactors,* Journal of American Ceramic Society, vol. 56, No. 2, pp. 36–41 (1973).

Roark, R. J. et al., *Formulas for Stress and Strain,* McGraw–Hill Book Company, New York, 5th ed. (1975), p. 506.

Technical Brochure for Applied Test Systems on Series 1101 Universal Testing Machine, (no date).

METHOD FOR TESTING THE STRENGTH AND STRUCTURAL INTEGRITY OF NUCLEAR FUEL PARTICLES

CONTRACTUAL ORIGIN OF THE INVENTION

The United States Government has rights in this invention pursuant to contract number DE-AC07-76ID01570 between the U.S. Department of Energy and EG&G Idaho, Inc., now contract number DE-AC07-94ID13223 between the U.S. Department of Energy and Lockheed Idaho Technologies Company.

BACKGROUND OF THE INVENTION

The present invention generally relates to a testing method for nuclear fuel materials, and more particular to a testing method for multi-component nuclear fuel particles which is characterized by a high level of accuracy and efficiency.

Recent developments in nuclear reactor technology have created a corresponding need for improved fuel materials having a high level of structural integrity. In particular (as discussed in further detail below), fuel particles have been developed for high temperature gas reactor systems (hereinafter known as "HTGR" systems) which involve small, substantially spherical particles (microspheres) having an average diameter of about 300–900 μm. Each of these particles includes a central core or center portion comprised of a fissionable radioactive material. In a preferred embodiment, this material will consist of $^{235}$UCO (uranium-235 carbonate). The center portion or central core of each particle is entirely covered/encapsulated by multiple protective layers preferably consisting of pyrolytic carbon, as well as at least one barrier layer preferably consisting of silicon carbide (SIC). The pyrolytic carbon layers are optimally applied by chemical vapor deposition using a conventional fluidized bed system. The SiC layer is preferably derived by the thermal decomposition of methyltrichlorosilane. The completed particles which incorporate the foregoing chemical compositions are often called "TRISO" particles, and are further discussed in the following references (incorporated herein by reference) which likewise discuss HTGR technology: Tennery, V. J., et al., "Structural Characterization of HTGR Pyrocarbon Fuel Particle Coatings", *J. Am. Ceram. Soc.*, 60(5–6):268–274(1977); Stinton, D. P., et al., "Effect of Deposition Conditions on the Properties of Pyrolytic SiC Coatings for HTGR Fuel Particles", *Ceramic Bulletin*, 57(6):568–573(1978); Krautwasser, P., et al., "Raman Spectral Characterization of Silicon Carbide Nuclear Fuel Coatings", *J. Am. Ceram. Soc.*, 66(6):424–433(1983); Smith, C. L., "SiC-Fission Product Reactions in HTGR TRISO $UC_2$ and $UC_xO_y$ Fissile Fuel: I., Kinetics of Reactions in a Thermal Gradient", *J. Am. Ceram. Soc.*, 62(11–12):600–606(1979); and Allen, P. L., et al., "Nuclear Fuel Coated Particle Development in the Reactor Fuel Element Laboratories of the U.K. Atomic Energy Authority", *Nucl. Technol.*, 35:246–253(1977). Furthermore, while the present invention shall be described herein with reference to a nuclear fuel particle containing a $^{235}$UCO center region with multiple pyrolytic carbon protective layers and at least one SiC barrier layer, the present invention may likewise be used in connection with nuclear fuel particles of comparable physical character/dimensions which contain other materials aside from those listed above. Further information regarding the physical, chemical, and structural character of nuclear fuel materials suitable for testing in accordance with the present invention shall be discussed in greater detail below.

Of particular importance regarding the use of nuclear fuel particles (e.g. particles having a radioactive core/center portion surrounded by at least one protective layer and at least one barrier layer) is the physical strength and integrity of each particle with emphasis on the barrier layer. As indicated above, a preferred barrier layer associated with HTGR fuel particles of the type described herein is comprised of SiC. This material is chemically characterized as a moderately brittle ceramic composition. The barrier layer is of particular importance since a significant amount of the strength and structural integrity of each fuel particle is directly attributable to the barrier layer associated therewith. In addition, the barrier layer is designed to retain fission products (e.g. xenon, krypton, carbon monoxide, cerium, cesium, and palladium) within each particle unit during use in an HTGR system. The presence of a weak and ineffective barrier layer in a nuclear fuel particle will diminish the strength/durability of the particle, and will also permit the leakage of fission products outwardly from the particle. For this reason, it is desirable to test the structural integrity of a particle sample before using a particular batch or supply of fuel particles within a selected reactor system. In this regard, the present invention involves a new and unique method for testing nuclear fuel particles as discussed in further detail below.

When nuclear fuel particles and brittle ceramic materials therein (e.g. SiC) are tested for mechanical strength, they exhibit a wide sample-to-sample variation in measured strength values. Strength distribution and stress analysis results are also affected by the selected test method. Many prior testing methods have been used to test the strength and structural integrity of "TRISO"-type nuclear fuel particles. For example, strength tests have been conducted using diametrical compression involving rings of SiC barrier layers removed from TRISO particles containing a center region comprised of $^{235}$UCO as discussed in Bongartz, K., et al., "The Brittle Ring Test: A Method for Measuring Strength and Young's Modulus on Coatings of HTR Fuel Particles", *J. Nucl. Mater.*, 62:123–137(1976). Testing as described in the foregoing article involved the production of ring sections from each test particle using parallel cuts through the particle. Compressive force was thereafter applied to each ring section until it fractured in order to generate information regarding stress characteristics of the ring section under consideration. However, in many instances involving the use of this procedure, structural damage occurred to the ring sections during removal from each particle. Ring sections damaged during processing (e.g. cutting and polishing) were thereafter discarded since they could not be effectively tested. As a result, data was lost for many ring sections, especially those having inherent defects or weaknesses which could have generated valuable comparative information. Furthermore, when an individual ring section is tested using diametrical compression, only a small portion of the inner barrier layer (e.g. SiC) associated with each particle is exposed to maximum tensile compression. A particular ring section may represent only 10% of a particle's SiC surface area. In this regard, the area under maximum tensile stress may be about 10% (or less) of the ring section. For any particle being tested, use of the foregoing test procedure will therefore expose only about 1% of a given particle to maximum stress levels. In contrast, when the selected fuel particles are actually used in a reactor system, the entire surface and volume of the barrier layer (SIC) is exposed to maximum stress levels.

Another testing technique is discussed in Gilchrist, K. E., et al., "A Technique for Measuring the Strength of High Temperature Reactor Fuel Particle Coatings", *J. Nucl. Mater.*, 43:347–350(1972). This technique involved a probability-based method designed to test the surface and interior volume of the barrier layer (SIC) in each particle. To implement this test, various portions of each test particle were physically removed (e.g. by cutting and the like), ultimately resulting in the preparation of a hollow hemispherical section from the particle. The hemispherical section was then cemented over a small hole in a metal (copper) plate and internally pressurized to determine the amount of pressure necessary to fracture the section. Further information regarding this technique is disclosed in Allen, P. L., et al. "Nuclear Fuel Coated Particle Development in the Reactor Fuel Element Laboratories of the U.K. Atomic Energy Authority", *Nuclear Technology*, 35:246–253(1977).

Finally, an additional method is disclosed in Minkato, K., et al., "Crushing Strength of Irradiated TRISO Coated Fuel Particles", *J. Nucl. Mater.*, 119:326–332(1983). The method disclosed in this reference (hereinafter referred to as the "point load test") involved a crush test designed to determine the strength of selected fuel particles. Specifically, individual particles were positioned between flat platens of hardened steel and compressed between the platens. This method is particularly characterized by a process in which limited portions of the selected fuel particle (e.g. those portions or "points" touching each flat platen) are exposed to stress levels compared with the present invention which more broadly distributes compressive forces. The considerable benefits associated with the broad distribution of compressive forces, as well as further technical and substantive comparisons between both methods will be discussed below.

The present invention involves a unique and highly efficient method which is characterized by numerous benefits compared with prior testing methods including but not limited to: (1) the avoidance of potentially-destructive process steps which involve the physical removal by cutting and the like of various sections of the selected fuel particles; (2) an absence of process steps involving the use of adhesive agents or other materials designed to retain various portions of test particles within the selected testing apparatus; and (3) the use of a process which more broadly distributes compressive forces over test particles, thereby resulting in more accurate, complete, and comprehensive data involving structural integrity, stress capability, and the like. In this regard, the present invention provides numerous advantages compared with prior methods in terms of effectiveness, accuracy, and simplicity. For this reason, the invention described herein represents an advance in the art of nuclear fuel testing as discussed in greater detail below.

SUMMARY OF THE INVENTION

It is an object of the present invention to a method for testing the strength and structural integrity of nuclear fuel particles which involves a minimal number of process steps and testing components/structures.

It is another object of the invention to provide a method for testing the strength and structural integrity of nuclear fuel particles which is readily undertaken in a rapid and efficient manner so that large numbers of test particles may be accurately and effectively analyzed.

It is another object of the invention to provide a method for testing the strength and structural integrity of nuclear fuel particles which is applicable to a wide variety of different nuclear fuel materials.

It is a further object of the invention to provide a method for testing the strength and structural integrity of nuclear fuel particles which avoids the destructive physical treatment of test particles (e.g. the removal by cutting and the like of large sections from each fuel particle).

It is a further object of the invention to provide a method for testing the strength and structural integrity of nuclear fuel particles which provides a controlled amount of compressive force to test particles in a highly accurate manner so that complete analytical results may be achieved.

It is a still further object of the invention to provide a method for testing the strength and structural integrity of nuclear fuel particles which involves the application of compressive force in a manner wherein the applied forces are widely distributed over each fuel particle. As a result, a significantly greater degree of testing accuracy is achieved compared with other methods including those which involve the application of compressive force to each particle at single points thereon.

It is an even further object of the invention to provide a method for testing the strength and structural integrity of nuclear fuel particles which avoids the use of complex testing equipment and chemical fixatives (e.g. adhesives) in the testing process.

In accordance with the foregoing objects, the present invention involves a highly efficient and unique method for testing the strength and structural integrity of nuclear fuel particles which are substantially spherical in configuration. In particular, the method described herein is particularly designed to test spherical fuel particles which individually comprise a center region of fissionable nuclear/radioactive material (e.g. $^{235}$UCO) and at least one barrier layer surrounding the center region. The barrier layer provides the nuclear fuel particle with a significant and dominant part of its structural integrity, and also maintains fission products within the particle during use in a selected reactor. An exemplary and preferred composition suitable for manufacturing the barrier layer will consist of SiC.

Each fuel particle comprises a hemispherical upper portion and a hemispherical lower portion, with the upper and lower portions being equal in size. In addition, each particle may likewise include at least one protective layer surrounding the barrier layer and/or beneath the barrier layer. Exemplary materials which may be used to construct each protective layer will consist of pyrolytic carbon and equivalent compositions. The protective layer or layers (especially those outside of the barrier layer) may be retained in position during testing of the selected particle or may optionally be removed as discussed below.

Regarding the construction materials used to manufacture the fuel particles, the present invention shall not be limited to the testing of any particular fuel materials and compositions associated therewith. Instead, many different types of nuclear fuel particles using different components/materials may be tested with an equal degree of efficiency.

In accordance with the invention, the fuel particle to be tested is first placed in a testing apparatus comprising an upper compression member and a lower compression member. In a preferred embodiment, each compression member will consist of a rigid and durable planar structure (e.g. constructed from stainless steel.) The upper compression member will preferably include a first pressure-exerting surface (optimally planar in construction) and at least one first depression therein beginning at the first pressure-exerting surface and extending inwardly into the upper compression member. As discussed in further detail below, the first depression is preferably circular in cross-section and sized to allow only part of the upper portion of the selected test particle therein while preventing entry of all of the upper portion into the first depression. Likewise, the lower compression member will include a second pressure-exerting surface (preferably planar in construction) and at least one second depression therein which is equal in size, shape, and configuration to the first depression. The second depression begins at the second pressure-exerting surface and extends inwardly into the lower compression member. The second depression is preferably circular in cross-section and sized to allow only part of the lower portion of the selected fuel particle therein while preventing entry of all of the lower portion into the second depression. The upper compression member and the lower compression member are positioned within the testing apparatus so that the first pressure-exerting surface faces the second pressure-exerting surface and is parallel thereto, with the first depression in the first pressure exerting-surface being directly above and in axial alignment with the second depression in the second pressure-exerting surface.

Thereafter, the selected fuel particle is positioned between the upper compression member and the lower compression member within the testing apparatus, with at least part of the upper portion of the fuel particle being positioned within the first depression in the upper compression member, and at least part of the lower portion of the fuel particle being positioned within the second depression in the lower compression member. As a result, the fuel particle is securely positioned between the upper and lower compression members in a manner which prevents the axial, rotational, and lateral movement thereof without the use of any auxiliary structural components or chemical fixatives (adhesives). Compressive forces may then be applied to the fuel particle in a highly efficient manner wherein the forces are broadly distributed relative to the test particle. As discussed below, the use of a system which allows the broad distribution of forces provides more accurate results compared with systems which distribute forces at discrete and singular points on the test particle.

After engagement of the selected particle within the testing apparatus and between the upper and lower compression members, the fuel particle is compressed between the compression members until it fractures. Compression within the testing apparatus is accomplished by movement of at least one of the upper and lower compression members toward and against the fuel particle at a preferred rate of about 0.002–0.004 inches per minute. Finally, the amount of compressive force which was needed by the testing apparatus to fracture the fuel particle is measured and recorded. This value provides important and accurate information regarding the strength and structural integrity of the fuel particle being tested. In addition, the force value necessary to fracture the particle may thereafter be mathematically converted into a tensile strength value which can then be plotted, characterized, and/or interpreted using one of many different standard statistical approaches.

An important aspect of the foregoing process involves proper formation of the first and second depressions within the upper and lower compression members. In addition, the testing apparatus should be configured to achieve the precise axial alignment and overhead orientation of the first depression relative to the second depression. The first and second depressions may be formed within the upper and lower compression members by manual processes including but not limited to machining and/or drilling of the upper and lower compression members as desired. Orientation of the first and second depressions may also be accomplished manually by selective manipulation of the upper and lower compression members within the testing apparatus. In an alternative embodiment, the first depression and second depression are formed in precise axial alignment by initially providing a depression-forming spherical member having a hardness level which exceeds that of the upper compression member and the lower compression member. As a result, deformation and/or fracturing of the spherical member is prevented when the spherical member is compressed between the upper and lower compression members as discussed below. For example, if the upper and lower compression members are constructed from stainless steel, an exemplary and preferred composition suitable for producing the depression-forming spherical member will consist of zirconia.

To properly form the first and second depressions, the spherical member is positioned within the testing apparatus and placed between the upper and lower compression members. Thereafter, the spherical member is compressed between the upper compression member and the lower compression member until it is pressed inwardly into the upper and lower compression members. As a result, the first depression is formed within the upper compression member and the second depression is formed within the lower compression member in a manner wherein the first depression is directly above and in precise axial alignment with the second depression. The spherical member is then removed from the testing apparatus, followed by insertion and testing of the selected fuel particle using the steps described above. This alternative method ensures that the first and second depressions are formed in a highly exact and accurate manner without the need for precise pre-testing alignment procedures.

The present invention enables highly accurate results to be achieved while avoiding the use of complex and intricate testing processes. In addition, implementation of the invention enables a broader distribution of compressive forces to each test particle so that widely-distributed flaws within the particle have a greater chance of detection and characterization compared with narrow-distribution compression systems. These benefits are achieved without removing portions of the test particle by cutting or other disruptive physical processes which can introduce additional flaws into the particle prior to testing. Finally, the present invention enables precise and secure immobilization of the fuel particle being tested without the use of extensive equipment and chemical fixative materials (e.g. adhesives). In this regard, the invention represents an advance in the art of nuclear fuel technology, and enables the testing of nuclear materials in a highly advanced and efficient manner.

These and other objects, features, and advantages of the present invention will be described below in the following Brief Description of the Drawings and Detailed Description of Preferred Embodiments.

BRIEF DESCRIPTION OF THE DRAWINGS

FIGS. 7A–7D involve sequential, partial cross-sectional views of a method for forming the first and second depressions in the upper and lower compression members of FIG. 5 using the depression-forming spherical member of FIG. 6.

DETAILED DESCRIPTION OF THE INVENTION

The present invention involves a unique and highly efficient method for testing the strength and structural integrity of nuclear fuel particles which are substantially spherical in shape and are typically characterized as "microspheres". As previously indicated, recent developments in nuclear energy have resulted in the production of high temperature gas reactor systems hereinafter designated as "HTGR" reactors. These reactors typically use nuclear fuel particles or microspheres of the type described above. To ensure that a supply of particles destined for use in an HTGR system will remain physically intact and viable during nuclear fission, it is desirable to test selected particle samples for strength and structural integrity. Adequate structural integrity and particle strength are likewise important to ensure that fission products are retained within the fuel particles during use. The leakage of fission products from the particles is undesirable because they are radioactive and could be detrimental to the health and safety of workers if released from the HTGR system. The specific fission products which are generated during the production of nuclear energy will vary, depending on the type of fissionable nuclear material being used in the particles. For example, fissionable nuclear material consisting of $^{235}$UCO (e.g. uranium-235 carbonate) will generate fission products consisting of $^{133}$Xe, $^{134}$Cs, $^{85m}$Kr, $^{105}$Pd, $^{134}$Ba, $^{144}$Ce, and others. Regarding strength and structural integrity levels, it is generally preferred that nuclear fuel particles selected for use in HTGR reactors be capable of withstanding applied forces (both internally and externally generated) that result in tensile stresses within the barrier (e.g. silicon carbide) layer of about 100–500 MPa. Stress concentrations due to irradiation-induced structural changes in the various carbon layers may, in fact, lead to stresses of up to about 2500 MPa. However, these values will necessarily vary in view of the particular nuclear fuel materials being used.

A. Nuclear Fuel Particles to be Tested

Figure 1:
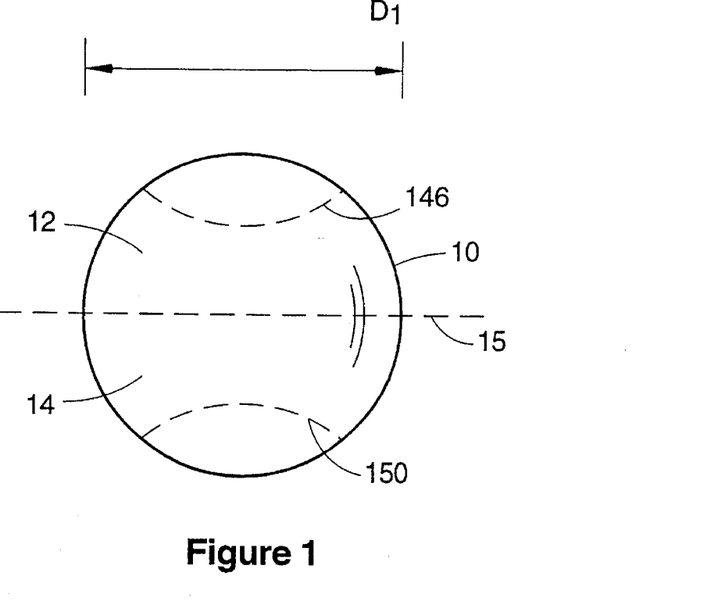
FIG. 1 is a schematic enlarged front perspective view of an exemplary nuclear fuel particle (microsphere) suitable for testing in accordance with the present invention.
Figure 2:
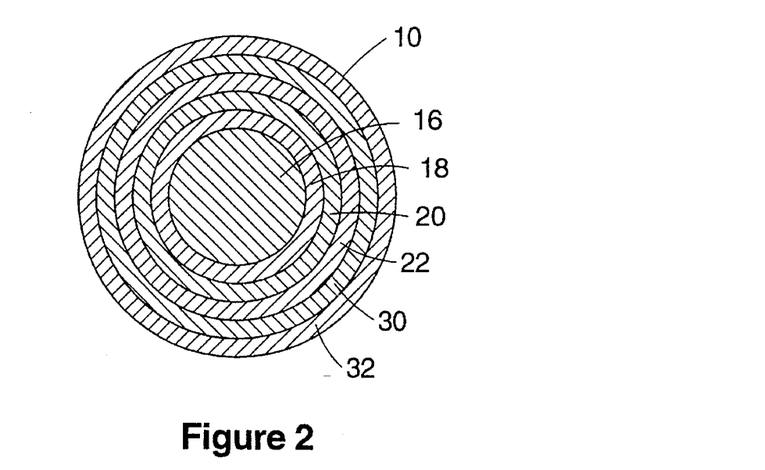
FIG. 2 is a schematic enlarged cross-sectional view of the fuel particle of FIG. 1 which illustrates the various layers and components of the particle in a preferred embodiment.

As noted above, the present invention shall not be limited to any particular nuclear materials, barrier layers, or protective layers in the nuclear fuel particles to be tested. In this regard, nuclear fuel particles/microspheres of many different types and compositions may be tested for strength and structural integrity. While the invention described below shall not be limited to any particular nuclear fuel particles, an exemplary nuclear fuel particle 10 is illustrated in FIGS. 1–2. With reference to FIGS. 1–2, a particle 10 substantially spherical in configuration is schematically shown which includes a hemispherical upper portion 12 and a hemispherical lower portion 14, with the upper portion 12 being equal in size to the lower portion 14. As illustrated in FIG. 1, the juncture where the upper portion 12 meets the lower portion 14 is shown at dashed dividing line 15. The particle 10 further includes a spherical center region 16 (FIG. 2) consisting of a selected fissionable radioactive (nuclear) composition. A preferred radioactive composition suitable for use in the center region 16 is a spherical portion of $^{235}$UCO (uranium-235 carbonate) having a diameter of about 200 μm. Other compositions suitable for use in the center region 16 include but are not limited to $^{235}$UC$_2$, $^{232}$ThC$_2$, and $^{239}$PuC$_2$, with a preferred diameter range for the center region 16 being about 200–600 μm. In tritium production systems, the center region 16 may consist of $^6$Li compounds (e.g. LiAl$_5$O$_8$ and LiAlO$_2$).

Surrounding the center region 16 in the particle 10 of FIG. 2 is a buffer layer 18 which is primarily designed to provide volume in order to retain fission or reaction gases (e.g. $^{133}$Xe, $^{85m}$Kr, and CO) within the particle 10. A preferred composition suitable for use as the buffer layer 18 consists of pyrolytic carbon applied by conventional fluidized bed chemical vapor deposition techniques at a uniform thickness of about 100 μm.

Also included within typical fuel particles suitable for use in HTGR reactors are one or more protective layers In the particle 10 of FIGS. 1–2, an inner protective layer 20 is provided which entirely surrounds the buffer layer 18. A preferred composition suitable for use as the inner protective layer 20 consists of pyrolytic carbon applied by conventional fluidized bed chemical vapor deposition techniques at a uniform thickness of about 40/m. The inner protective layer 20 is likewise designed to retain fission gases and other fission/reaction products within the particle 10, and also provides added strength.

Entirely surrounding the inner protective layer 20 within the particle 10 is least one barrier layer 22 which, in the embodiment of FIGS. 1–2, is manufactured from SiC (silicon carbide) at a uniform thickness of about 35 μm. The barrier layer 22 generally provides the nuclear fuel particle 10 with a significant and dominant part of its structural integrity, and serves to function as the primary barrier regarding the escape of fission/reaction products from the particle 10 during use in a reactor. In a preferred embodiment involving the use of SiC as the barrier layer 22, the SiC is typically applied in a conventional manner by the thermal decomposition of methyltrichlorosilane. Other compositions suitable for use as the barrier layer 22 include but are not limited to ZrC, HfC, TaC, NbC, Si$_3$N$_r$, SiAlON, and AlN applied conventionally at a uniform thickness of about 30–60 μm.

Entirely surrounding the barrier layer 22 is an outer protective layer 30. A preferred composition suitable for use as the outer protective layer 30 again consists of pyrolytic carbon applied by conventional fluidized bed chemical vapor deposition techniques at a uniform thickness of about 40 μm. The outer protective layer 30 is again designed to retain fission gases and other fission/reaction products within the particle 10, and also provides some additional strength.

Finally, the particle 10 shown in FIGS. 1–2 includes an optional external coating 32 which preferably consists of a still further layer of pyrolytic carbon applied by fluidized bed chemical vapor deposition techniques at a uniform thickness of about 45 μm. The external coating 32 is designed to minimize damage to the particle 10 during handling and the like.

The particle 10 illustrated in FIGS. 1–2 has a diameter D (FIG. 1) of about 360 μm. In accordance with FIGS. 1–2, the diameter $D_1$ of the particle 10 shall be equivalent to the maximum width of the particle 10 as taken at the juncture between the hemispherical upper portion 12 and hemispherical lower portion 14 shown at dashed line 15 in FIG. 1.

However, the present invention shall not be limited to particles having any particular dimensional characteristics, with most nuclear fuel particles of interest having diameter values ranging from about 300– 900 μm. The particle 10 shown in FIGS. 1–2 and described above which involves a center region 16 manufactured from $^{235}$UCO and a barrier layer 22 comprised of SiC is conventionally known as a "TRISO" particle. This type of particle will normally have the following characteristics as indicated below in TABLE I:

TABLE I

| Property | Mean Value |
| --- | --- |
| Total uranium (wt. %) | >87.0 |
| $^{235}$U enrichment (wt. %) | 93.15 (+0.15, −1.00) |
| Carbon/uranium atomic ratio | >0.5 |
| Oxygen/uranium atomic ratio | 1.4–1.7 |
| Density (Mg/m$^3$) | ≥10.3 |

However, as noted above, the present invention shall not be limited to nuclear fuel particles having the foregoing components and numerical parameters. Other fuel particles involving different characteristics and components may also be tested in accordance with the invention. Exemplary fuel particles of the type described herein which can be tested using the methods described below are available from the following commercial sources: General Atomics, Inc. of San Diego, Calif. (U.S.A.); British Nuclear Fuels, Plc of Salwick Preston, UK; CEGA, Inc. of San Diego, Calif. (U.S.A.); Babcock & Wilcox, Inc. of Lynchburg, Va. (U.S.A.); Kernforschungsanlage, Julich GmbH of Julich, Germany; and NFS of Erwin, Tenn. (U.S.A.).

As previously noted, further information regarding HTGR systems and nuclear fuel particles used in HTGR systems is described in the following articles which are incorporated herein by reference: Tennery, V. J., et al., "Structural Characterization of HTGR Pyrocarbon Fuel Particle Coatings", *J. Am. Ceram. Soc.*, 60(5–6):268–274(1977); Stinton, D. P., et al., "Effect of Deposition Conditions on the Properties of Pyrolytic SiC Coatings for HTGR Fuel Particles", *Ceramic Bulletin*, 57(6):568–573(1978); Krautwasser, P., et al., "Raman Spectral Characterization of Silicon Carbide Nuclear Fuel Coatings", *J. Am. Ceram. Soc.*, 66(6):424–433(1983); Smith, C. L., "SiC-Fission Product Reactions in HTGR TRISO UC$_2$ and UC$_x$O$_y$ Fissile Fuel: I., Kinetics of Reactions in a Thermal Gradient", *J. Am. Ceram. Soc.*, 62(11–12):600–606(1979); and Allen, P. L., et al., "Nuclear Fuel Coated Particle Development in the Reactor Fuel Element Laboratories of the U.K. Atomic Energy Authority", *Nucl. Technol.*, 35:246–253(1977).

B. Testing Methods

A main goal of the present invention is to provide a highly efficient testing method which avoids the need to perform physical dissection of the test particles while enabling the distribution of compressive forces over a broad area on each particle. As a result, more comprehensive and sensitive testing of individual particles for widely-distributed internal flaws is provided. Further information regarding benefits of the present invention compared with prior test methods is provided below.

Figure 3:
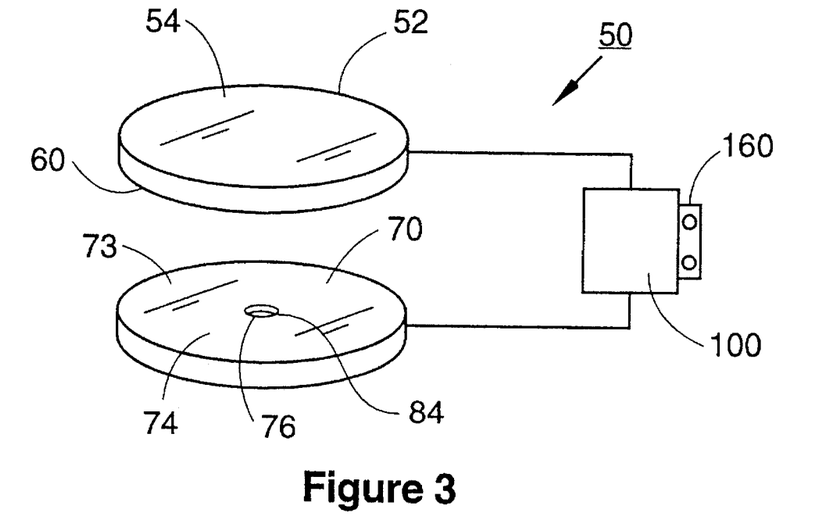
FIG. 3 is a schematic, partial perspective view of a testing apparatus which includes upper and lower compression members suitable for conducting strength/structural integrity tests on nuclear fuel particles of the type shown in FIGS. 1–2.
Figure 4:
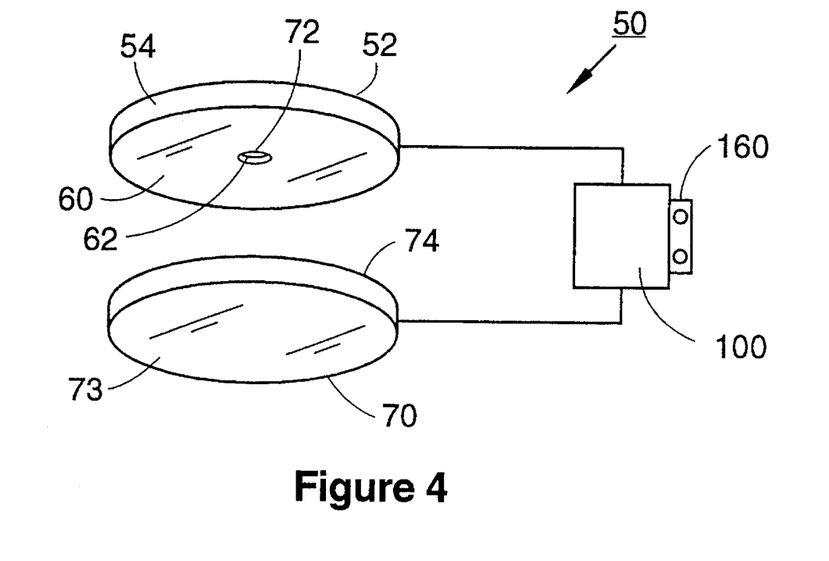
FIG. 4 is a schematic, partial perspective view of the testing apparatus of FIG. 3 from a different angle which specifically illustrates the first pressure-exerting surface of the upper compression member.
Figure 5:
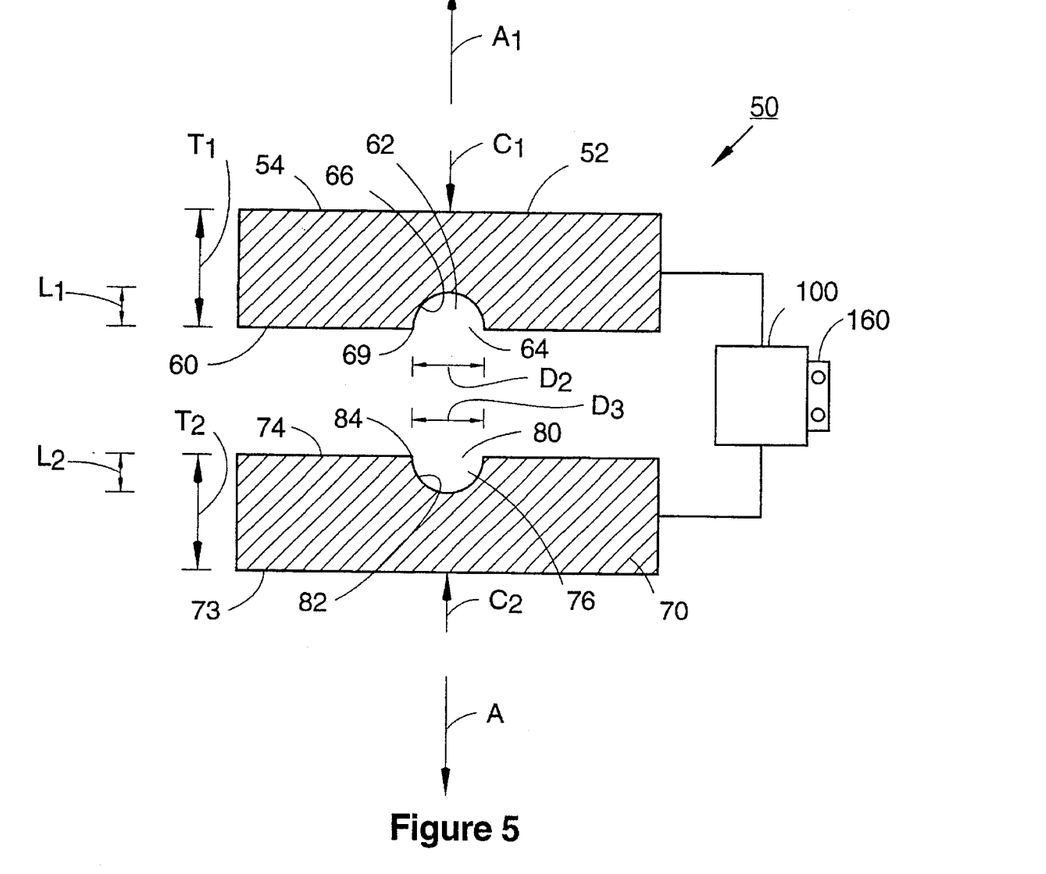
FIG. 5 is an enlarged schematic cross-sectional view of the upper and lower compression members in the testing apparatus of FIGS. 3–4 wherein the first and second depressions are illustrated.

With reference to FIGS. 3–5, a testing apparatus 50 is provided which may involve may different forms as discussed herein. However, key elements of the testing apparatus 50 include an upper compression member 52 which preferably comprises a planar disk-type structure 54 which is circular in cross-section. Regardless of form, the compression member 52 is manufactured from a material having a hardness level greater than that of the particle 10 described above (or any other nuclear fuel particles being tested by the apparatus 50). In a preferred embodiment, the upper compression member 52 is comprised of Type 304 stainless steel (especially if a "TRISO"-type particle of the composition described above is to be tested). Other materials suitable for use in connection with the upper compression member 52 include but are not limited to (1) other chromium-nickel stainless steels such as Type 316, Type 201, Type 310, and Type 347; (2) plain carbon steels such as Type 1010 through Type 1095; (3) alloy steels such as Type 1330, Type 2330, Type 3130, Type 4130, and Type 4140; and (4) hard ceramic materials such as alumina, zirconia, silicon carbide, and silicon nitride. In this regard, production of the upper compression member 52 shall not be limited to any particular construction material, provided that the selected material has a hardness level which exceeds that of the fuel particle (e.g. particle 10) being tested or consists of a stiff metal that can be indented, with the area surrounding the indent being strain hardenable during indentation.

While the upper compression member 52 shown in FIGS. 3–4 is illustrated in the form of disk-type structure 54, the compression member 52 may be configured in a wide variety of different forms including but not limited to planar, elongate structures which are square or rectangular in shape. Accordingly, the present invention shall not be limited to any specific shape or configuration regarding the upper compression member 52.

The selected upper compression member 52 will optimally have a thickness T (FIG. 5) which exceeds the diameter of the particle being tested in the apparatus 50 (e.g. diameter $D_1$ of particle 10 shown in FIG. 1). In addition, as specifically illustrated in FIG. 4, the upper compression member 52 includes an external first pressure-exerting surface 60 (preferably planar in configuration) which faces downwardly in the testing apparatus 50 as shown in FIGS. 3–5. Positioned at a selected location on the first pressure-exerting surface 60 (preferably at the center line C of the upper compression member 52 shown in FIG. 5) is at least one first dimple or depression 62. The first depression 62 (which is optimally hemispherical in configuration as illustrated) begins at the first pressure-exerting surface 60 and extends inwardly into the upper compression member 52 (FIG. 5). Within the upper compression member 52, the first depression 62 includes an internal cavity 64 which is surrounded by a continuous interior side wall 66 of annular design (e.g. circular in cross-section).

With reference to FIG. 5, the presence of first depression 62 within the upper compression member 52 results in the formation of a circular rim portion 69 at a position where the first pressure-exerting surface 60 meets the interior side wall 66 of the depression 62. The first depression 62 is circular in cross-section along its entire length. In addition, the maximum diameter $D_2$ of the first depression 62 (which consists of the diameter of the depression 62 at the first pressure-exerting surface 60 as shown in FIG. 5) will be less than the diameter of the selected fuel particle being tested (e.g. diameter $D_1$ of particle 10). In a preferred embodiment, the diameter $D_2$ of the first depression 62 will be about 30–60% of the diameter of the fuel particle of interest (e.g. diameter $D_1$ of particle 10), with an exemplary diameter $D_1$ range being about 60–600 μm. As a result, the first depression 62 is sized to allow only part of the hemispherical upper portion 12 of fuel particle 10 therein (e.g. within the internal cavity 64) while preventing entry of all of the portion 12 into the first depression 62 as described in further detail below. Furthermore, it is preferred that the length (e.g. depth) $L_1$ of the first depression 62 be less than the diameter of the selected fuel particle (e.g. diameter $D_1$ of particle 10). These design features are of substantial importance in the present invention as described below.

Also provided within the testing apparatus 50 as particularly illustrated in FIGS. 3 and 5 is a lower compression member 70 which is substantially identical to the upper compression member 52 in function, form, construction materials, dimensions, and purpose. In a preferred embodiment, the lower compression member 70 preferably comprises a planar disk-type structure 73 which is circular in cross-section. Regardless of form, the lower compression member 70 is optimally manufactured from a material having a hardness level equivalent to that of the upper compression member 52 and greater than the hardness of the particle 10 described above (or any other nuclear fuel particles being tested by the apparatus 50). In a preferred embodiment, the upper compression member 70 is again comprised of Type 304 stainless steel (especially if a "TRISO"-type particle of the composition described above is being tested). Other materials suitable for use in manufacturing the lower compression member 70 include but are not limited to (1) other chromium-nickel stainless steels such as Type 316, Type 201, Type 310, and Type 347; (2) plain carbon steels such as Type 1010 through Type 1095; (3) alloy steels such as Type 1330, Type 2330, Type 3130, Type 4130, and Type 4140; and (4) hard ceramic materials such as alumina, zirconia, silicon carbide, and silicon nitride. In this regard, production of the lower compression member 70 shall not be limited to any particular construction material, provided that the selected material has a hardness level which exceeds that of the fuel particle being tested (e.g. particle 10) or consists of a stiff metal that can be indented, with the area surrounding the indent being strain hardenable during indentation.

While the lower compression member 70 shown in FIGS. 3–4 is illustrated in the form of disk-type structure 73, the lower compression member 70 may be configured in a wide variety of different forms including but not limited to planar structures which are square or rectangular in shape. The configuration of the lower compression member 70 should preferably correspond with the selected shape of the upper compression member 52. Nonetheless, the present invention shall not be limited to any specific shape or configuration regarding the upper and lower compression members 52, 70.

The selected lower compression member 70 will optimally have a thickness $T_2$ (FIG. 5) which exceeds the diameter of the particle being tested in the apparatus 50 (e.g. diameter $D_1$ of particle 10 shown in FIG. 1). In addition, the lower compression member 70 includes an external second pressure-exerting surface 74 (preferably planar in configuration) which faces upwardly in the testing apparatus 50 as illustrated in FIGS. 3 and 5. Positioned at a selected location on the second pressure-exerting surface 74 (preferably at the center line $C_2$ of the lower compression member 70 shown in FIG. 5) is at least one second dimple or depression 76. The second depression 76 (which is optimally hemispherical in configuration) begins at the second pressure-exerting surface 74 and extends inwardly into the lower compression member 70 as illustrated in FIG. 5. Within the lower compression member 70, the second depression 76 includes an internal cavity 80 which is surrounded by a continuous interior side wall 82 of annular design (e.g. circular in cross-section). In a preferred embodiment, the second depression 76 will be equal in size, shape, internal volume, depth, and overall configuration to the first depression 62.

As illustrated in FIG. 5, the presence of the second depression 76 in the lower compression member 70 results in the formation of a circular rim portion 84 at a position where the second pressure-exerting surface 74 meets the interior side wall 82 of the second depression 76. The second depression 76 is also circular in cross-section along its entire length. In addition, the maximum diameter $D_3$ of the second depression 76 (which involves the diameter of the second depression 76 at the second pressure-exerting surface 74 as illustrated in FIG. 5) will be less than the diameter of the selected fuel particle being tested (e.g. diameter $D_1$ of particle 10). Likewise, the diameter $D_3$ of the second depression 76 will be optimally be equal to the diameter $D_2$ of the first depression 62. In a preferred embodiment, the diameter $D_3$ of the second depression 76 will be about 30–60% of the diameter of the fuel particle of interest (e.g. diameter $D_1$ of particle 10), with an exemplary diameter $D_3$ range being about 60–600 μm. As a result, the second depression 76 is sized to allow only part of the hemispherical lower portion 14 of fuel particle 10 therein (e.g. within the internal cavity 80) while preventing entry of all of the lower portion 14 into the second depression 76. Furthermore, it is preferred that the length (e.g. depth) $L_2$ of the second depression 76 (FIG. 5) be less than the diameter of the selected fuel particle (e.g. diameter $D_1$ of particle 10) and equal to the length (depth) $L_1$ of the first depression 62. These design features are of substantial importance in the present invention as discussed below.

With reference to FIG. 5, the upper and lower compression members 52, 70 are positioned within the testing apparatus 50 so that they are precisely parallel to and spaced apart from each other. In this manner, the first pressure-exerting surface 60 associated with the upper compression member 52 and the second pressure-exerting surface 74 associated with the lower compression member 70 are parallel to and spaced apart from each other, with the first pressure-exerting surface 52 directly facing the second pressure-exerting surface 74. It is also important that the first depression 62 is directly above and in axial alignment with the second depression 76. The term "axial alignment" as used herein shall involve a geometric relationship in which the longitudinal axis $A_1$ of the first depression 62 (FIG. 5) is in precise axial alignment with the longitudinal axis $A_2$ of the second depression 76. In this manner as discussed below, the fuel particle 10 (or any other selected fuel particle) may be precisely aligned within the testing apparatus 50 so that compressive force can be applied to the particle in a uniformly-distributed manner.

To apply compressive force to the selected particle (e.g. particle 10), the upper and lower compression members 52, 70 within the testing apparatus 50 are operatively connected to a force delivery system which is schematically illustrated in FIGS. 3–5 at reference number 100. The selected force delivery system 100 is designed to move at least one of the upper compression member 52 and lower compression member 70 toward a test particle (e.g. particle 10) placed between the compression members 52, 70 during a test procedure. For example, when fuel particle 10 (or any other test particle) is positioned between the upper and lower compression members 52, 70 as described below, the selected force delivery system 100 could apply compressive force to the particle 10 in the following ways: (1) movement of the upper compression member 52 downward against the particle 10 with the lower compression member 70 remaining stationary; (2) movement of the lower compression member 70 upward against the particle 10 with the upper compression member 52 remaining stationary; or (3) simultaneous movement of the upper compression member 52 downward and the lower compression member 70 upward with the particle 10 compressed therebetween. In this regard, the present invention shall not be limited to any particular compression mode regarding the testing apparatus 50 and compression members 52, 70.

Regarding the type of force delivery system 100 which is suitable for use in the testing apparatus 50, many different commercially-available systems may be employed for this purpose which include mechanical actuator mechanisms for moving at least one of the upper and lower compression members 52, 70 as described above. Likewise, the selected system 100 will include an integral measurement monitoring system for determining the amount of force being applied to the selected particle between the compression members 52, 70 during a test procedure. A representative commercial apparatus having all of these features which may be used as the force delivery system 100 is manufactured by Applied Test Systems, Inc. of Butler Pa. (U.S.A.) under the designation "Series 1101". This system is designed to incorporate the upper and lower compression members 52, 70 therein so that the selected particle (e.g. particle 10) can be compressed in a manner which allows the amount of applied force to be precisely monitored. As a result, force levels necessary to cause fracturing of a test particle can be determined.

The commercial system described above (e.g. Series 1101 unit produced by Applied Test Systems, Inc.-[hereinafter "ATS"]) consists of a screw-driven universal-type compression testing apparatus. It is designed to move the upper compression member 52 in a downward direction using a screw-drive system, with the lower compression member 70 remaining in a fixed position. The system has a 1000 lb. capacity with a twin screw drive assembly, manually-adjustable limit switches, automatic overload protection, and an automatic break detector regarding the object being tested. The system is designed to operate so that the upper compression member 52 therein can be moved within a speed range of 0.002–20.0 inches per minute, with a speed accuracy of about ±1.0%. The system further includes a universal-type load cell having an accuracy rating of ±0.1% of range, or ±0.5% of indicated load. The load cell in the system is associated with a microprocessor-based load module having four load ranges, digital display, 0–10 VDC output, peak load recall, and overload protection. Also included in the system is a crosshead displacement display unit which includes an incremental encoder in connection with a resolution of 0.0001 in. over the full range of travel. Ranges within the system include 0.2, 2.0, 10.0, and 20.0 in. full scale. In accordance with these features, the foregoing system is capable of applying a controlled compressive load to test fuel particles and thereafter indicating measuring the amount of compressive force needed to fracture a given particle between the compression members 52, 70. As further described below, the upper compression member 52, the lower compression member 70, and the structural features thereof (e.g. axially-aligned depressions 62, 76) are unique and provide highly accurate test results which are not achieved by prior test methods.

Regarding the type of apparatus which may be used as the force delivery system 100, many different commercially-available stress-testing systems can be employed for this purpose other than the specific system listed above. In this regard, the present invention shall not be exclusively limited to any particular system for this purpose. Devices which are suitable for use as the force delivery system 100 (e.g. for controlled movement of the upper compression member 52 and/or lower compression member 70) are conventional in nature and commercially available from many other sources including but not limited to Instron Corporation of Canton, Mass. (U.S.A.); Tinius Olsen Testing Machine Co., Inc. of Willow Grove, Pa. (U.S.A.); United Calibration Corp. of Garden Grove, Calif. (U.S.A.); MTS Systems Corp. of Minneapolis, Minn. (U.S.A.); and W. C. Dillon Corp. of Van Nuys, Calif. (U.S.A.). Accordingly, the force delivery system 100 shall not be limited to the ATS Series 1101 system which is provided for example purposes. Other conventional systems may be used in an equally-effective manner provided that they are capable of moving the upper compression member 52 and/or lower compression member 70 in a controlled manner with the ability to generate and display quantitative force data.

Regarding preparation of the first depression 62 and the second depression 76, many different production methods may be employed. In this regard, the present invention shall not be exclusively limited to any particular process for producing the depressions 62, 76 within the upper and lower compression members 52, 70. For example, the depressions 62, 76 may be manually produced using conventional processing techniques including but not limited to drilling and machining using standard industrial equipment. Thereafter, the upper and lower compression members 52, 70 are manually aligned to ensure that the first depression 62 is directly above and in axial alignment with the second depression 76 (e.g. axis $A_1$ of the first depression 62 is aligned with axis $A_2$ of the second depression 76 as shown in FIG. 5). In a preferred embodiment as described above, the first depression 62 is optimally placed at the center line $C_1$ of the upper compression member 52, with the second depression 76 being positioned at the center line $C_2$ of the lower compression member 70. However, the present invention shall not be limited to this particular configuration. The first and second depressions 62, 76 can be located at any respective position on the upper and lower compression members 52, 70 provided that the depressions 62, 76 are axially aligned when used to test a selected fuel particle (e.g. particle 10). It should also be noted that the present invention shall not be limited to a testing apparatus 50 which includes only a single pair of first and second depressions 62, 76 within the upper compression member 52 and the lower compression member 70. Other systems may be used in which multiple pairs of depressions are employed, provided that each pair includes one depression in the upper compression member 52 which is axially aligned with a corresponding depression in the lower compression member 70.

Figure 6:
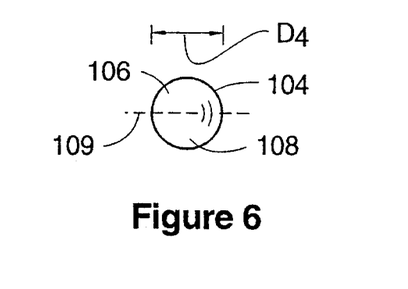
FIG. 6 is a front perspective view of a depression-forming spherical member used to form the first and second depressions in the upper and lower compression members of FIG. 5.

In an alternative embodiment, a highly efficient method is disclosed herein for producing the first and second depressions 62, 76 which avoids manual production processes while enabling precise axial alignment between the first depression 62 and the second depression 76. With reference to FIG. 6, a depression-forming spherical member 104 is provided which comprises a hemispherical upper section 106 and a hemispherical lower section 108, with the lower section 108 being equal in size to the upper section 106. The upper section 106 meets the lower section 108 at the juncture represented in FIG. 6 by dashed line 109. The spherical member 104 has a diameter $D_4$ as illustrated in FIG. 6 which is optimally less than the diameter of the selected fuel particle or particles to be tested in accordance with the invention (e.g. less than the diameter $D_1$ of the particle 10). In a preferred embodiment, the diameter $D_4$ of the spherical member 104 will be about 30–60% less than the diameter of the particle or particles to be tested. Exemplary $D_4$ diameter values for the spherical member 104 will be about 60–600 µm, although the present invention shall not be limited to this range which is provided for example purposes.

A method for producing the first and second depressions 62, 76 within the upper and lower compression members 52, 70 using the spherical member 104 is illustrated in FIGS. 7A–7D. To implement the method of FIGS. 7A–7D, the material used to produce the spherical member 104 should have a hardness level which exceeds the hardness of the upper and lower compression members 52, 70. A higher level of hardness associated with the spherical member 104 is necessary to prevent substantial deformation and/or fracturing of the spherical member 104 when compressed between compression members 52, 70 to produce the depressions 62, 76 as discussed below. In this regard, the composition used to manufacture the spherical member 104 may vary, depending on the materials used to construct the upper and lower compression members 52, 70. In a preferred embodiment wherein the upper and lower compression members 52, 70 are made of Type 304 stainless steel, the spherical member 104 is optimally manufactured from zirconia of a type consisting of 96% zirconia partially stabilized with about 4% yttrium oxide. Other compositions which may be used to produce the spherical member 104 include but are not limited to zirconia partially stabilized with calcia or magnesia, iron carbide, alumina, silicon carbide, or silicon nitride. These materials are suitable for use in connection with the list of compositions described above for producing the upper and lower compression members 52, 70. However, the precise construction materials to be used in producing the spherical member 104 may be determined in accordance with preliminary pilot tests on the particular compositions selected for use in manufacturing the upper and lower compression members 52, 70.

Figure 7A:
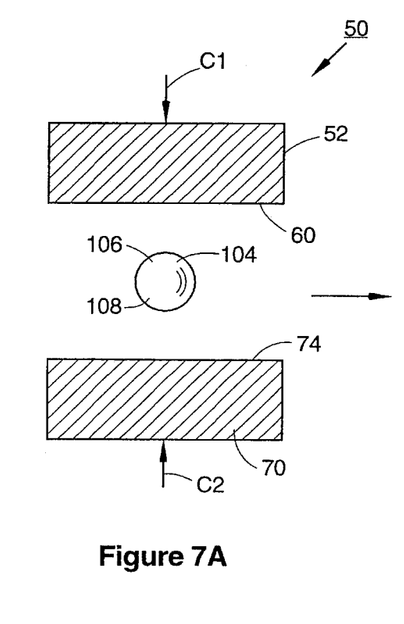

To form the first and second depressions 62, 76 in a highly efficient manner, the spherical member 104 is positioned in the testing apparatus 50 and placed between the upper compression member 52 and the lower compression member 70 (FIG. 7A). In a preferred embodiment, the upper section 106 of the spherical member 104 will be directly adjacent to, below, and in substantial alignment with the center line C of the upper compression member 52. Likewise, the lower section 108 of the spherical member 104 will be directly adjacent to, above, and in substantial alignment with the center line $C_2$ of the lower compression member 70. At all times during production of the first and second depressions 62, 76 (regardless of which method is used), the first pressure-exerting surface 60 of the upper compression member 52 should be maintained in a parallel relationship with the second pressure-exerting surface 74 of the lower compression member 70 to ensure proper formation of the depressions 62, 76.

Figure 7B:
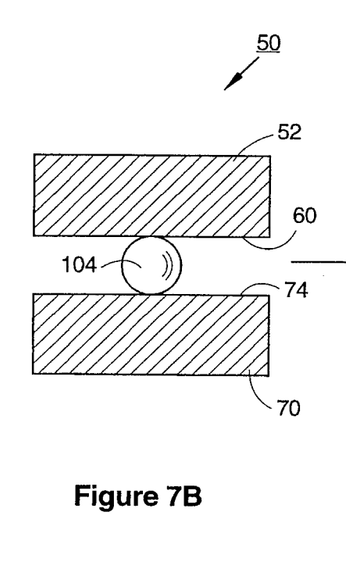

Once the spherical member 104 is properly positioned in the testing apparatus 50 as described above, the force delivery system 100 (FIGS. 3–5) associated with the apparatus 50 is activated. As a result, the spherical member 104 is compressed between the upper and lower compression members 52, 70 as illustrated in FIG. 7B. Compression of the spherical member 104 using the force delivery system 100 to move the compression members 52, 70 may be undertaken by (1) movement of the upper compression member 52 against the spherical member 104 while the lower compression member 70 remains stationary; (2) movement of the lower compression member 70 against the spherical member 104 while the upper compression member 52 remains stationary; or (3) movement of the upper and lower compression members 52, 70 simultaneously against the spherical member 104. The type of compression mode to be selected will depend on the particular force delivery system 100 chosen for use in the present invention.

Figure 7D:
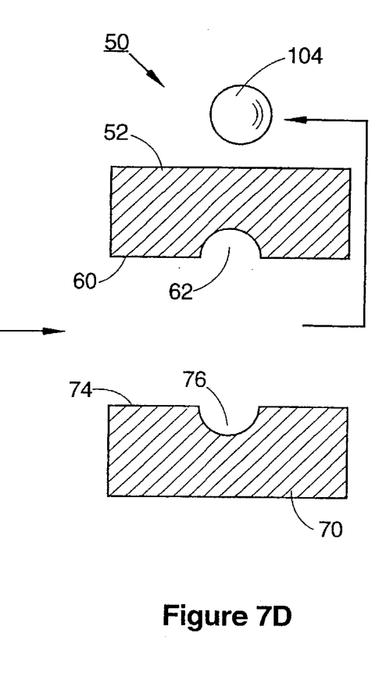

Compression of the spherical member 104 between the upper and lower compression members 52, 70 in the foregoing manner is allowed to continue until the spherical member 104 is pressed inwardly into the compression members 52, 70 as shown in FIG. 7C. As a result, the upper section 106 of the spherical member 104 is pressed into the first pressure-exerting surface 60 and upper compression member 52 to produce the first depression 62. Likewise, the lower section 108 of the spherical member 104 is pressed into the second pressure-exerting surface 74 and lower compression member 70 to produce the second depression 76. Formation of the first and second depressions 62, 76 in this manner is accomplished by the greater hardness level of the spherical member 104 compared with the upper and lower compression members 52, 70. Furthermore, this method may be used to produce first and second depressions 62, 76 of a different size (e.g. depth) as may be desired for particular applications in connection with specific fuel particles of interest. To produce first and second depressions 62, 76 of a particular depth (e.g. L and $L_2$ as shown in FIG. 5), compression of the spherical member 104 illustrated in FIGS. 7B–7C is allowed to continue until depressions of the desired configuration (depth) are achieved. In the embodiment of FIG. 7 (and in most embodiments of concern) the compression process can be allowed to continue until the upper compression member 52 meets (e.g. substantially contacts) the lower compression member 70 (FIG. 7C). However, variable degrees of compression and displacement of the upper and lower compression members 52, 70 can be used to produce depressions 62, 76 of different size and depth as desired. In a preferred embodiment involving the materials recited herein (e.g. a zirconia spherical member 104, stainless steel upper and lower compression members 52, 70, as well as the other compositions/components described above), production of the depressions 62, 76 will involve the application of about 448–1779N of force to the spherical member 104. However, exact production parameters will depend on the particular materials being used within the testing apparatus 50 (e.g. the type of spherical member 104) and the size of the fuel particle to be tested. In this regard, the present invention shall not be limited regarding the exemplary embodiment shown in FIGS. 7A–7D.

The final step associated with the depression-forming process involves separation of the upper and lower compression members 52, 70 from each other within the testing apparatus 50 and removal of the spherical member 104 therefrom (FIG. 7D). As a result, the first and second depressions 62, 76 may be formed in a highly efficient manner with a precise degree of axial alignment. These results are rapidly achieved using a minimal amount of equipment while avoiding manual alignment procedures. It should likewise be noted that, if desired, multiple pairs of depressions may be formed in the foregoing manner by using more than one spherical member 104 during the compression process (e.g. one spherical member 104 for each pair of depressions in the upper and lower compression members 52, 70).

Having formed the first depression 62 and second depression 76 within the upper and lower compression members 52, 70, testing of the selected fuel particle (e.g. particle 10) may now be undertaken. While the present invention is applicable in connection with a wide variety of different fuel particles and compositions, the process described below shall be presented relative to particle 10 for example purposes.

Figure 8A:
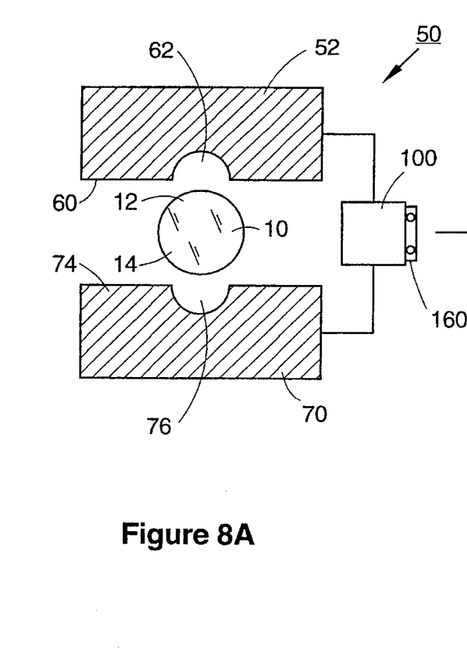
FIGS. 8A–8C involve sequential, partial cross-sectional views of the upper and lower compression members of FIG. 5 during use in connection with the testing of a nuclear fuel particle of the type illustrated in FIGS. 1–2.
Figure 8B:
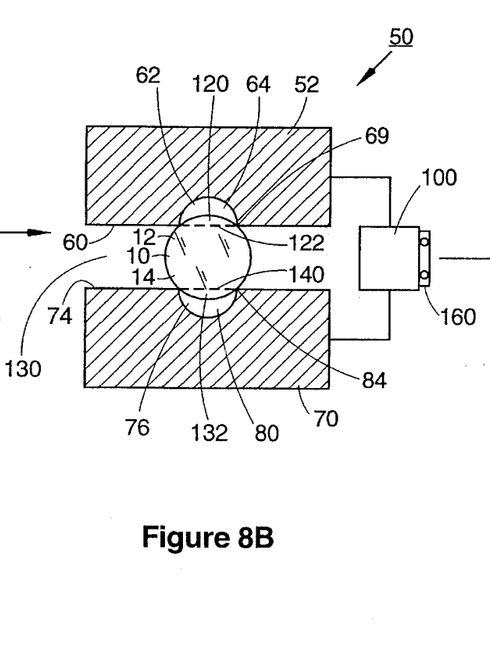
Figure 8C:
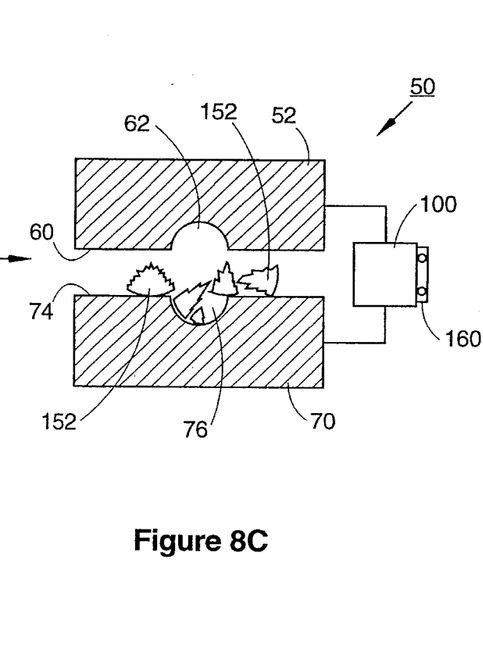

With reference to FIGS. 8A–8C, the testing method of the present invention is schematically illustrated. As shown in FIG. 8A, the particle 10 is initially placed within the testing apparatus 50 between the upper and lower compression members 52, 70. At this point during the testing process, the upper and lower compression members 52, 70 are spaced apart from each other in a amount sufficient to permit placement of the particle 10 therebetween (e.g. an amount in excess of the diameter D associated with the particle 10). To avoid the introduction of any extraneous structural defects in the particle 10 prior to testing, it is handled carefully with a minimal amount of physical manipulation. In certain cases as determined by preliminary pilot studies on the fuel particles of interest, layers of material surrounding the barrier layer in the test particle may be removed thermally (e.g. by burning) or through the use of chemical etchants. For example, regarding particle 10, the outer protective layer 30 and external coating 32 which are both comprised of carbon could be removed by burning in a conventional furnace at a temperature of about 900° C. to expose the underlying barrier layer 22 (made of SIC). Thereafter, any oxidized materials which remain on the barrier layer 22 could be removed using a chemical etchant (e.g. hydrofluoric acid). However, the present invention shall not be limited to any particle configuration, and shall not be dependent on the presence or absence of material layers which cover the barrier layer in a test particle. The barrier layer in the selected test particle (e.g. layer 22 in particle 10) is responsible for a predominant portion of the strength and structural integrity associated with the particle. In many cases, the removal of layers covering the barrier layer 22 will provide a more direct placement of the designated load on the barrier layer 22, thereby facilitating a more direct calculation of stress values. However, a determination regarding the removal of layers covering the barrier layer 22 will depend on a variety of factors as indicated by preliminary pilot testing.

As illustrated in FIG. 8A, the particle 10 is placed within the testing apparatus 50 so that the upper portion 12 thereof is aligned with and directly below the first depression 62 in the upper compression member 52, with the lower portion 14 of particle 10 being aligned with and directly above the second depression 76 in the lower compression member 70. Thereafter, at least one of the upper compression member 52 and the lower compression member 70 is moved toward and against the particle 10 by the force delivery system 100 so that the compression members 52, 70 are positioned as illustrated in FIG. 8B. As previously indicated, placement of the particle 10 in the position shown in FIG. 8B and subsequent compression of the particle 10 is accomplished by (1) movement of the upper compression member 52 toward and against the particle 10 in a downwardly direction with the lower compression member 70 remaining in a stationary position; (2) movement of the lower compression member 70 toward and against the particle 10 in an upward direction with the upper compression member 52 remaining in a stationary position; or (3) movement of the upper compression member 52 and lower compression member 70 simultaneously toward and against the particle 10. The exact mode of compression to be employed will depend on the type of force delivery system 100 selected for use in any given case, with the present invention not being limited to any particular force delivery system 100 or compression mode.

As illustrated in FIG. 8B, the particle 10 is firmly maintained in position between the upper compression member 52 and the lower compression member 70. Specifically, part of the upper portion 12 of the particle 10 (e.g. section 120 in FIG. 8B above dashed line 122) is positioned within the upper depression 62. Accordingly, section 120 of the particle 10 is located within the internal cavity 64 of the first depression 62 and beneath the first pressure-exerting surface 60. The remainder of the upper portion 12 of particle 10 is located outside of the depression 62 and within gap 130 between the upper compression member 52 and lower compression member 70 (FIG. 8B). As a result, entry of the entire upper portion 12 into the first depression 62 is prevented, with the upper portion 12 being only partially positioned within the first depression 62. Likewise, part of the lower portion 14 of the particle 10 (e.g. section 132 in FIG. 8B below dashed line 140) is positioned within the lower depression 76. In this manner, section 132 of the particle 10 is located within the internal cavity 80 of the second depression 76 and beneath the second pressure-exerting surface 74. The remainder of the lower portion 14 of particle 10 is located outside of the depression 76 and within gap 130 between the upper and lower compression members 52, 70. Once again, entry of the entire lower portion 14 into the second depression 76 is prevented as illustrated in FIG. 8B, with the lower portion 14 being only partially positioned within the second depression 76. This configuration provides numerous benefits compared with other stress application systems (e.g. those which do not use the dual depressions of the present invention and instead involve planar structures which apply force at discrete (single) points on the particle of interest). In particular, the method of the present invention enables a broader distribution of compressive forces and a resultant broad distribution of maximum tensile stresses within the barrier layer of each particle being tested, thereby providing more accurate results and greater detection of widely-dispersed defects. The depression-based system described herein also prevents axial, lateral, and rotational slippage of the particle being tested compared with point-type compression systems. This factor likewise contributes to improved accuracy and testing efficiency.

Next, as illustrated in FIG. 8C, compressive force is applied to the particle 10 by movement of at least one of the upper compression member 52 and lower compression member 70 against the particle 10 as described above. This process in undertaken by the force delivery system 100 in a conventional manner as previously indicated. During compression of the particle 10, the circular rim portion 69 associated with the upper compression member 52 (which is formed at the juncture between the first pressure-exerting surface 60 and side wall 66 of depression 62) forcibly engages the upper portion 12 of the particle 10. As a result, compressive force is broadly applied to the upper portion 12 of the particle 10 in a circular pattern which circumferentially surrounds the particle 10 as illustrated in FIG. 1 at curved dashed line 146. In certain cases which depend on the character of the particle 10 being tested (as well as the type of upper compression member 52 being used), the particle 10 and/or rim portion 69 may actually deform in a slight manner prior to fracturing of the particle 10 as force is applied thereto. Accordingly, the circular force pattern applied to the upper portion 12 of the particle 10 may be somewhat broader and more spread out (widely distributed) than the discrete application of force schematically illustrated at single dashed line 146 in FIG. 1. Regardless of whether this phenomenon occurs, the force pattern applied to the upper portion 12 of the particle 10 in accordance with the invention will provide all of the unique benefits previously described and further discussed below.

During compression of the particle 10, the circular rim portion 84 associated with the lower compression member 70 (which is formed at the juncture between the second pressure-exerting surface 74 and side wall 82 of depression 76) forcibly engages the lower portion 14 of the particle 10. Accordingly, compressive force is broadly applied to the lower portion 14 of the particle 10 in a circular pattern which circumferentially surrounds the particle 10 as illustrated in FIG. 1 at curved dashed line 150. In certain cases which again depend on the character of the particle 10 being tested (as well as the type of lower compression member 70 being used), the particle 10 and/or rim portion 84 may actually deform in a slight manner prior to fracturing of the particle 10 as force is applied thereto. As a result, the circular force pattern applied to the lower portion 14 of the particle 10 may be somewhat broader and more spread out (widely distributed) than the discrete application of force schematically illustrated at single dashed line 150 in FIG. 1. Regardless of whether this phenomenon occurs, the force pattern applied to the lower portion 14 of the particle 10 will provide all of the unique benefits previously described and further discussed below.

Compression of the particle 10 in the foregoing manner continues at a gradual rate until fracturing takes place. Regardless whether the upper compression member 52, the lower compression member 70, or both move against the particle 10, movement of these components is undertaken at a preferred rate of about 0.002–0.004 inches minute. As soon as the particle 10 reaches its maximum stress capacity, it fractures into multiple fragments 152 illustrated schematically in FIG. 8C. Immediately upon fracturing in this manner, the application of compressive force (e.g. movement of the upper compression member 52 and/or lower compression member 70) within the testing apparatus 50 is stopped either manually or automatically, depending on the type of commercial force delivery system 100 being used. When fracturing occurs, the force value necessary to fracture the particle 10 (typically in Newtons) is obtained measured from the force delivery system 100 which integrally includes a monitoring sub-system 160 designed to display the force value of concern. Such a monitoring sub-system 160 is a standard component of commercially available force delivery systems which are suitable for use in the present invention as discussed above (including the ATS Series 1101 system previously described).

At this point, the testing process is completed. The fragments 152 can thereafter be viewed using scanning electron microscopy for detailed observation of fracture patterns and identification of metallic inclusions therein. Chemical analysis of the fragments 152 can also be undertaken using many techniques including but not limited to electron dispersive spectroscopy (EDS) to provide additional information regarding the test particles and defects associated with the particles. The resulting force data can then be interpreted, manipulated, plotted, statistically configured, and otherwise used in many different conventional ways as desired. In this regard, the present invention shall not be limited to any particular use or treatment of data received using the foregoing process. Further information regarding data interpretation will be discussed below.

C. Benefits and Advantages—Data Manipulation

The present invention which involves placement of the selected fuel particle within first and second depressions 62, 76 in the upper and lower compression members 52, 70 provides numerous benefits compared with "point-type" compression systems and "ring-type" systems described above. The method disclosed herein enables the testing of whole fuel particles without dissecting and removing portions of the particles to be tested. As a result, the possibility of introducing additional defects into the particles prior to testing is avoided. Also, the present invention may test particles in a highly rapid manner without undesired axial, rotational, or lateral movement of the particles between the compression members within the testing apparatus. Furthermore, engagement of the selected particles within the testing apparatus is undertaken without the need for adhesives or other chemical fixatives. Because the method of the present invention enables testing in a rapid and efficient manner without the need for extensive manual alignment procedures, strength statistics can be rapidly gathered on hundreds of particles so that failure probabilities at low stresses may be measured with a minimum amount of extrapolation. Finally, and of considerable importance compared with point-type testing systems, the method described herein provides a wide distribution of the contact load through the surface and interior volume of the barrier (e.g. SiC) layer in each test particle so that strength statistics reflect a combination of both surface and volume flaws. Compared with point-type tests, the present invention is characterized by a much higher probability of flaw detection due to broader exposure of the particles (and barrier layers therein) to high stress levels. For these reasons, the method of the present invention represents a significant advance in the art of nuclear fuel particle testing, especially in connection with multi-layer particles of the type described above.

The data obtained using the foregoing process may be manipulated and interpreted in many different ways. For example, the compressive force needed to fracture the test particle can be mathematically converted to a tensile strength (stress) value. This is accomplished through the use of commercial finite element computer software packages (e.g. products sold under the name "ABAQUS" (version 4.9) by Hibbett, Karlsson, & Sorenson of Providence, R.I. (U.S.A.) and "PATRAN" (version 2.4) by PDA Engineering of Costa Mesa, Calif. (U.S.A.). Furthermore, the probability that a given fuel particle out of a group of particles will fracture can be calculated by the proper application of "weakest link statistics" as discussed in Quinn, G. D., "Strength and Proof Testing", *Engineering Materials Handbook*, Vol. 4, p. 585–598, ASM International (1991) which is incorporated herein by reference. One specific functional form (mathematical expression of probability of failure as a function of strength) that can be used to represent these statistics involves a process conventionally known as "Weibull Statistical Analysis". Weibull techniques and expressions suitable for interpreting force data in accordance with the invention, as well as other information involving stress analysis in ceramic materials, are discussed and outlined in Trustrum, A. G., et al., "Applicability of Weibull Analysis for Brittle Materials", *J. Mater. Sci.*, 18:2765–2770 (1983); Richerson, D. W., Modern Ceramic Engineering, Marcel Dekker, Inc., New York, Ch. 15, pp. 662–679 (1982); and Evans, A. G., Fracture in Ceramic Materials, Noyes Publications, Park Ridge, N.J., Ch. 15, pp. 364–402 (1984), all of which are incorporated herein by reference. Regardless of which mathematical expression is used during curve fitting procedures, a large number of samples (fuel particles) should be tested to achieve accurate estimates of failure probabilities at low stress levels. The testing of about 500–1000 particles in any given situation will provide adequate results. The use of substantial numbers of test particles produces data for very weak particles in the test group and therefore minimizes extrapolation of the data curves to low probabilities. Testing a large number of particles will also indicate whether there is a small population of particular flaws which are more harmful to overall strength and structural integrity levels compared with the majority of more common flaws. Evidence of different flaw populations can be demonstrated by a group of data points with a different slope on a Weibull plot involving the following expression: ln ln[1/1–probability of failure]v. ln of strength. Particular evidence of different flaw populations often becomes obvious as a "dog leg" configuration to the left within the foregoing plot at low strength levels or to the right at high strength levels. If an insufficient number of tests are made, mean strength values can be extrapolated by using a straight line into the low-strength region of the plot.

There are numerous methods, approaches, and techniques for interpreting data generated from the compression testing process of the present invention. In this regard, the invention shall not be limited to any statistical methods in connection with data generated as described above.

The present invention represents an advance in the art of nuclear fuel testing, and solves numerous problems uniquely associated with the testing of fuel particles. Having herein described preferred embodiments of the invention, it is anticipated that suitable modifications may be made thereto by individuals skilled in the relevant art which nonetheless remain within the scope of the invention. The present invention shall therefore only be construed in accordance with the following claims:

I claim:

1. A method for testing the strength and structural integrity of nuclear fuel particles by applying compressive force thereto comprising the steps of:

providing a nuclear fuel particle comprising a hemispherical upper portion and a hemispherical lower portion, said lower portion being equal in size to said upper portion, said fuel particle further comprising a center region and at least one barrier layer surrounding said center region, said center region comprising at least one radioactive composition therein;

placing said fuel particle within a testing apparatus comprising an upper compression member and a lower compression member, said upper compression member comprising a first pressure-exerting surface and at least one first depression therein, said first depression beginning at said first pressure-exerting surface and extending inwardly into said upper compression member, said first depression being circular in cross-section and sized to allow only part of said upper portion of said fuel particle therein while preventing entry of all of said upper portion into said first depression, said lower compression member comprising a second pressure-exerting surface and at least one second depression therein, said second depression beginning at said second pressure-exerting surface and extending inwardly into said lower compression member, said second depression being circular in cross-section and sized to allow only part of said lower portion of said fuel particle therein while preventing entry of all of said lower portion into said second depression, said upper compression member and said lower compression member being positioned within said testing apparatus so that said first pressure-exerting surface faces said second pressure-exerting surface, said first pressure-exerting surface being parallel to and spaced apart from said second pressure-exerting surface with said first depression being directly above and in axial alignment with said second depression;

positioning said fuel particle between said upper compression member and said lower compression member within said testing apparatus, with said upper portion of said fuel particle being partially positioned within said first depression in said upper compression member and said lower portion of said fuel particle being partially positioned within said second depression in said lower compression member;

compressing said fuel particle between said upper compression member and said lower compression member within said testing apparatus until said fuel particle fractures; and measuring how much compressive force was needed to fracture said fuel particle during said compressing of said fuel particle by said testing apparatus.

2. The method of claim 1 wherein said compressing of said fuel particle between said upper compression member and said lower compression member comprises the step of moving at least one of said upper compression member and said lower compression member toward and against said fuel particle at a rate of about 0.002–0.004 inches per minute.

3. The method of claim 1 wherein said center region of said fuel particle is comprised of $^{235}$UCO and said barrier layer is comprised of SiC.

4. The method of claim 1 wherein said fuel particle further comprises at least one protective layer surrounding and covering said barrier layer, said method further comprising the step of removing said protective layer which surrounds and covers said barrier layer prior to said positioning of said fuel particle between said upper compression member and said lower compression member.

5. The method of claim 1 further comprising the step of mathematically converting said compressive force needed to fracture said fuel particle into a tensile strength value.

6. A method for testing the strength and structural integrity of nuclear fuel particles by applying compressive force thereto comprising the steps of:

providing a fuel particle comprising a hemispherical upper portion and a hemispherical lower portion, said lower portion being equal in size to said upper portion, said fuel particle further comprising a center region and at least one barrier layer surrounding said center region, said center region being comprised of $^{235}$UCO and said barrier layer being comprised of SiC;

placing said fuel particle within a testing apparatus comprising an upper compression member and a lower compression member, said upper compression member comprising a first pressure-exerting surface and at least one first depression therein, said first depression beginning at said first-pressure exerting surface and extending inwardly into said upper compression member, said first depression being circular in cross-section and sized to allow only part of said upper portion of said fuel particle therein while preventing entry of all of said upper portion into said first depression, said lower compression member comprising a second pressure-exerting surface and at least one second depression therein, said second depression beginning at said second pressure-exerting surface and extending inwardly into said lower compression member, said second depression being circular in cross-section and sized to allow only part of said lower portion of said fuel particle therein while preventing entry of all of said lower portion into said second depression, said upper compression member and said lower compression member being positioned within said testing apparatus so that said first pressure-exerting surface faces said second pressure-exerting surface, said first pressure-exerting surface being parallel to and spaced apart from said second pressure-exerting surface with said first depression being directly above and in axial alignment with said second depression;

positioning said fuel particle between said upper compression member and said lower compression member within said testing apparatus, with said upper portion of said fuel particle being partially positioned within said first depression in said upper compression member and said lower portion of said fuel particle being partially positioned within said second depression in said lower compression member;

compressing said fuel particle between said upper compression member and said lower compression member within said testing apparatus until said fuel particle fractures, said compressing of said fuel particle between said upper compression member and said lower compression member comprising moving at least one of said upper compression member and said lower compression member toward and against said fuel particle at a rate of about 0.002–0.004 inches per minute; and measuring how much compressive force was needed to fracture said fuel particle during said compressing of said fuel particle by said testing apparatus.

7. The method of claim 6 further comprising the step of mathematically converting said compressive force needed to fracture said fuel particle into a tensile strength value.

8. The method of claim 6 wherein said fuel particle further comprises at least one protective layer surrounding and covering said barrier layer, said method further comprising the step of removing said protective layer which surrounds and covers said barrier layer prior to said positioning of said fuel particle between said upper compression member and said lower compression member.

9. A method for testing the strength and structural integrity of nuclear fuel particles by applying compressive force thereto comprising the steps of:

providing a depression-forming spherical member and a nuclear fuel particle, said nuclear fuel particle comprising a hemispherical upper portion and a hemispherical lower portion, said lower portion being equal in size to said upper portion, said fuel particle further comprising a center region and at least one barrier layer surrounding said center region, said center region being comprised of radioactive material;

positioning said spherical member within a testing apparatus comprising an upper compression member and a lower compression member, said upper compression member comprising a first pressure-exerting surface, and said lower compression member comprising a second pressure-exerting surface, said upper compression member and said lower compression member being positioned within said testing apparatus so that said first pressure-exerting surface faces said second pressure-exerting surface, with said first pressure-exerting surface being parallel to and spaced apart from said second pressure-exerting surface, said spherical member being harder than said upper compression member and said lower compression member in order to prevent deformation and fracturing of said spherical member when compressed between said upper compression member and said lower compression member;

placing said spherical member between said upper compression member and said lower compression member within said testing apparatus;

compressing said spherical member between said upper compression member and said lower compression member until said spherical member is pressed inwardly into said upper compression member and said lower compression member, said compressing of said spherical member forming at least one first depression beginning at said first pressure-exerting surface of said upper compression member and extending inwardly into said upper compression member, and at least one second depression beginning at said second pressure-exerting surface of said lower compression member and extending inwardly into said lower compression member, said first depression being circular in cross-section and sized to allow only part of said upper portion of said fuel particle therein while preventing entry of all of said upper portion into said first depression, with said second depression being circular in cross section and sized to allow only part of said lower portion of said fuel particle therein while preventing entry of all of said lower portion into said second depression, said first depression being directly above and in axial alignment with said second depression; removing said spherical member from said testing apparatus;

positioning said fuel particle between said upper compression member and said lower compression member within said testing apparatus, with said upper portion of said fuel particle being partially positioned within said first depression in said upper compression member and said lower portion of said fuel particle being partially positioned within said second depression in said lower compression member;

compressing said fuel particle between said upper compression member and said lower compression member within said testing apparatus until said fuel particle fractures; and measuring how much compressive force was needed to fracture said fuel particle during said compressing of said fuel particle by said testing apparatus.

10. The method of claim 9 wherein said compressing of said fuel particle between said upper compression member and said lower compression member comprises the step of moving at least one of said upper compression member and said lower compression member toward and against said fuel particle at a rate of about 0.002–0.004 inches per minute.

11. The method of claim 9 wherein said center region of said fuel particle is comprised of $^{235}$UCO and said barrier layer is comprised of SiC.

12. The method of claim 9 wherein said fuel particle further comprises at least one protective layer surrounding and covering said barrier layer, said method further comprising the step of removing said protective layer which surrounds and covers said barrier layer prior to said positioning of said fuel particle between said upper compression member and said lower compression member.

13. The method of claim 9 further comprising the step of mathematically converting said compressive force needed to fracture said fuel particle into a tensile strength value.

14. A method for testing the strength and structural integrity of nuclear fuel particles by applying compressive force thereto comprising the steps of:

providing a depression-forming spherical member and a nuclear fuel particle, said nuclear fuel particle comprising a hemispherical upper portion and a hemispherical lower portion, said lower portion being equal in size to said upper portion, said fuel particle further comprising a center region and at least one barrier layer surrounding said center region, said center region being comprised of $^{235}$UCO and said barrier layer being comprised of SiC;

positioning said spherical member within a testing apparatus comprising an upper compression member and a lower compression member, said upper compression member comprising a first pressure-exerting surface, and said lower compression member comprising a second pressure-exerting surface, said upper compression member and said lower compression member being positioned within said testing apparatus so that said first pressure-exerting surface faces said second pressure-exerting surface, with said first pressure-exerting surface being parallel to and spaced apart from said second pressure-exerting surface, said spherical member being harder than said upper compression member and said lower compression member in order to prevent deformation and fracturing of said spherical member when compressed between said upper compression member and said lower compression member;

placing said spherical member between said upper compression member and said lower compression member within said testing apparatus;

compressing said spherical member between said upper compression member and said lower compression member until said spherical member is pressed inwardly into said upper compression member and said lower compression member, said compressing of said spherical member forming at least one first depression beginning at said first pressure-exerting surface of said upper compression member and extending inwardly into said upper compression member, and at least one second depression beginning at said second pressure-exerting surface of said lower compression member and extending inwardly into said lower compression member, said first depression being circular in cross-section and sized to allow only part of said upper portion of said fuel particle therein while preventing entry of all of said upper portion into said first depression, with said second depression being circular in cross-section and sized to allow only part of said lower portion of said fuel particle therein while preventing entry of all of said lower portion into said second depression, said first depression being directly above and in axial alignment with said second depression; removing said spherical member from said testing apparatus;

positioning said fuel particle between said upper compression member and said lower compression member within said testing apparatus, with said upper portion of said fuel particle being partially positioned within said first depression in said upper compression member and said lower portion of said fuel particle being partially positioned within said second depression in said lower compression member;

compressing said fuel particle between said upper compression member and said lower compression member within said testing apparatus until said fuel particle fractures, said compressing of said fuel particle between said upper compression member and said lower compression member comprising moving at least one of said upper compression member and said lower compression member toward and against said fuel particle at a rate of about 0.002–0.004 inches per minute; and measuring how much compressive force was needed to fracture said fuel particle during said compressing of said fuel particle by said testing apparatus.

15. The method of claim 14 wherein said fuel particle further comprises at least one protective layer surrounding and covering said barrier layer, said method further comprising the step of removing said protective layer which surrounds and covers said barrier layer prior to said positioning of said fuel particle between said upper compression member and said lower compression member.

16. The method of claim 14 further comprising the step of mathematically converting said compressive force needed to fracture said fuel particle into a tensile strength value.

* * * * *